United States Patent

Furutani et al.

Patent Number: 5,962,117
Date of Patent: Oct. 5, 1999

[54] LUBRICATING AGENT AND MAGNETIC RECORDING MEDIUM COMPRISING THE SAME

[75] Inventors: Takahiro Furutani, Otokuni-gun; Sayaka Shinomoto, Kyoto; Kazushi Miyata, Mishima-gun, all of Japan

[73] Assignee: Hitachi Maxell, Ltd., Osaka-fu, Japan

[21] Appl. No.: 09/004,168

[22] Filed: Jan. 2, 1998

Related U.S. Application Data

[62] Division of application No. 08/708,542, Sep. 5, 1996, Pat. No. 5,759,968.

[30] Foreign Application Priority Data

Sep. 5, 1995 [JP] Japan .................................. 7-254618

[51] Int. Cl.$^6$ ...................................................... G11B 5/71
[52] U.S. Cl. .................. 428/219; 428/421; 428/694 TF; 428/694 TP; 428/694 BF; 428/900
[58] Field of Search .................................. 508/517, 527; 428/421, 219, 694 TF, 694 TP, 694 BF, 900

[56] References Cited

U.S. PATENT DOCUMENTS

| | | | |
|---|---|---|---|
| 2,886,590 | 5/1959 | Montgomery et al. | 508/497 |
| 4,079,084 | 3/1978 | Houghton | 260/615 |
| 4,735,848 | 4/1988 | Kondo et al. | |
| 4,766,153 | 8/1988 | Casciani | 560/186 |
| 4,828,924 | 5/1989 | Shoji et al. | 428/422 |
| 4,839,067 | 6/1989 | Jansen | 252/11 |
| 5,073,280 | 12/1991 | Rossio et al. | 252/49.3 |
| 5,091,269 | 2/1992 | Kondo et al. | 428/694 TF |
| 5,214,216 | 5/1993 | Tohzuka et al. | |
| 5,556,707 | 9/1996 | Usuki et al. | 428/421 |

FOREIGN PATENT DOCUMENTS

| | | |
|---|---|---|
| 0 233 774 | 8/1987 | European Pat. Off. |
| 62-236118 | 10/1987 | Japan . |
| 1-308242 | 12/1989 | Japan . |
| 2-210615 | 8/1990 | Japan . |
| 7-65352 | 3/1995 | Japan . |

OTHER PUBLICATIONS

Chemical Abstracts RN 139360–39–7 (Date unknown).

*Primary Examiner*—Stevan A. Resan
*Attorney, Agent, or Firm*—Birch, Stewart, Kolasch & Birch, LLP

[57] ABSTRACT

A lubricating agent contains at least one alkylene oxide derivative having an alkylene oxide group and an ester moiety or an ammonium salt moiety, which is represented by the following general formula (1), (2), (3) or (4):

$$R^1-O-(R^2O)_m-R^3-COO-R^4 \quad (1)$$

$$R^1-O-(R^2O)_m-R^3-COONH_3-R^4 \quad (2)$$

$$R^4-OCO-R^3-O-(R^2O)_m-R^3-COO-R^4 \quad (3)$$

$$R^4-NH_3OCO-R^3-O-(R^2O)_m-R^3-COONH_3-R^4 \quad (4)$$

wherein
$R^1$ is a hydrocarbon group having 1 to 26 carbon atoms or a hydrogen atom,
$R^2$ is a hydrocarbon group having 1 to 6 carbon atoms,
$R^3$ is a hydrocarbon group having 1 to 26 carbon atoms,
$R^4$ is a hydrocarbon or fluorocarbon group having 1 to 26 carbon atoms, and
m is from 1 to 12.

There is also disclosed a magnetic recording medium having a non-magnetic substrate and a magnetic layer provided on at least one surface of the substrate, wherein the magnetic layer has the lubricating agent in or on the magnetic layer.

5 Claims, 4 Drawing Sheets

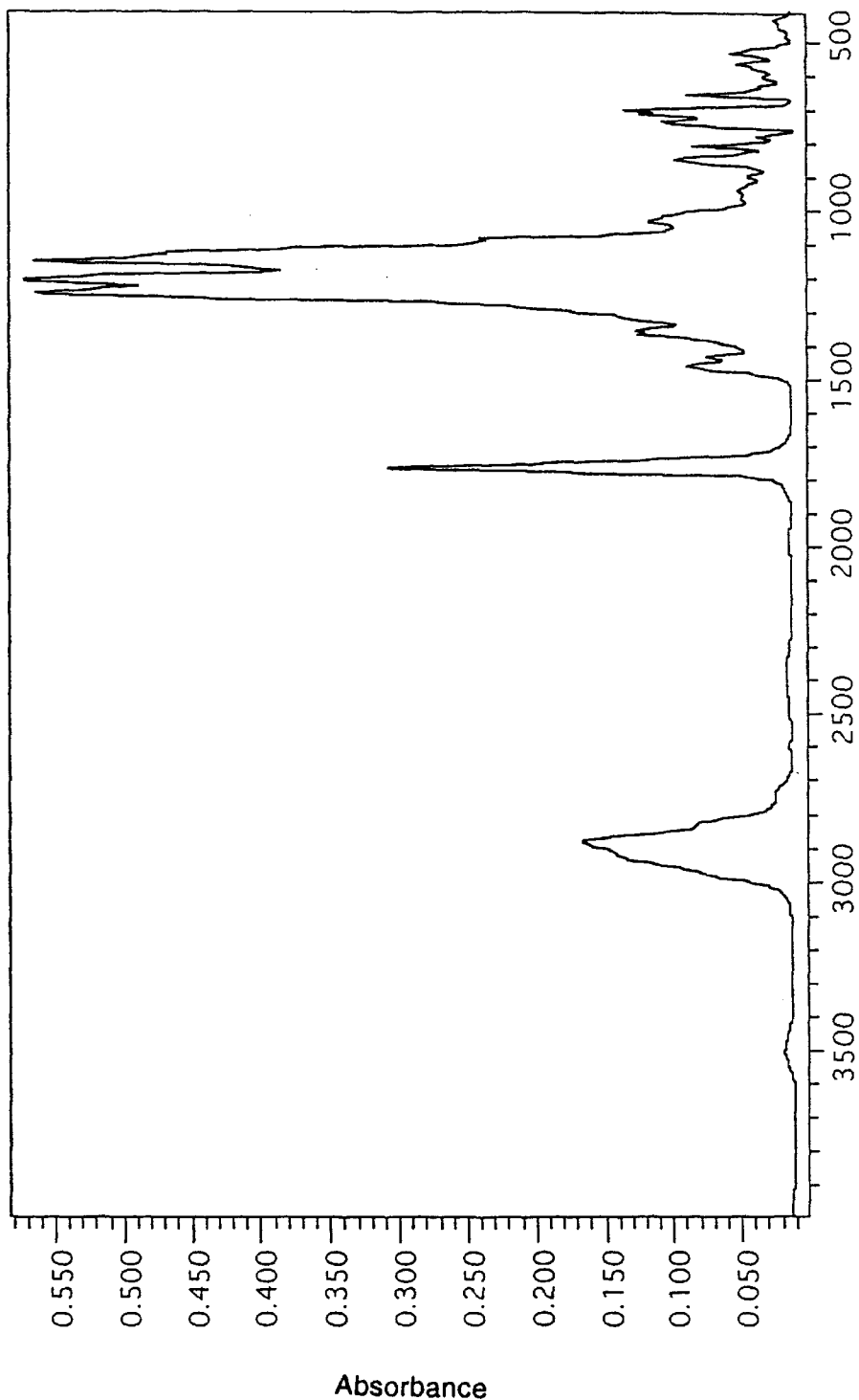
Fig. 1 IR Spectrum of $CH_3O(CH_2CH_2O)_2CH_2COOCH_2CH_2(CF_2)_6F$

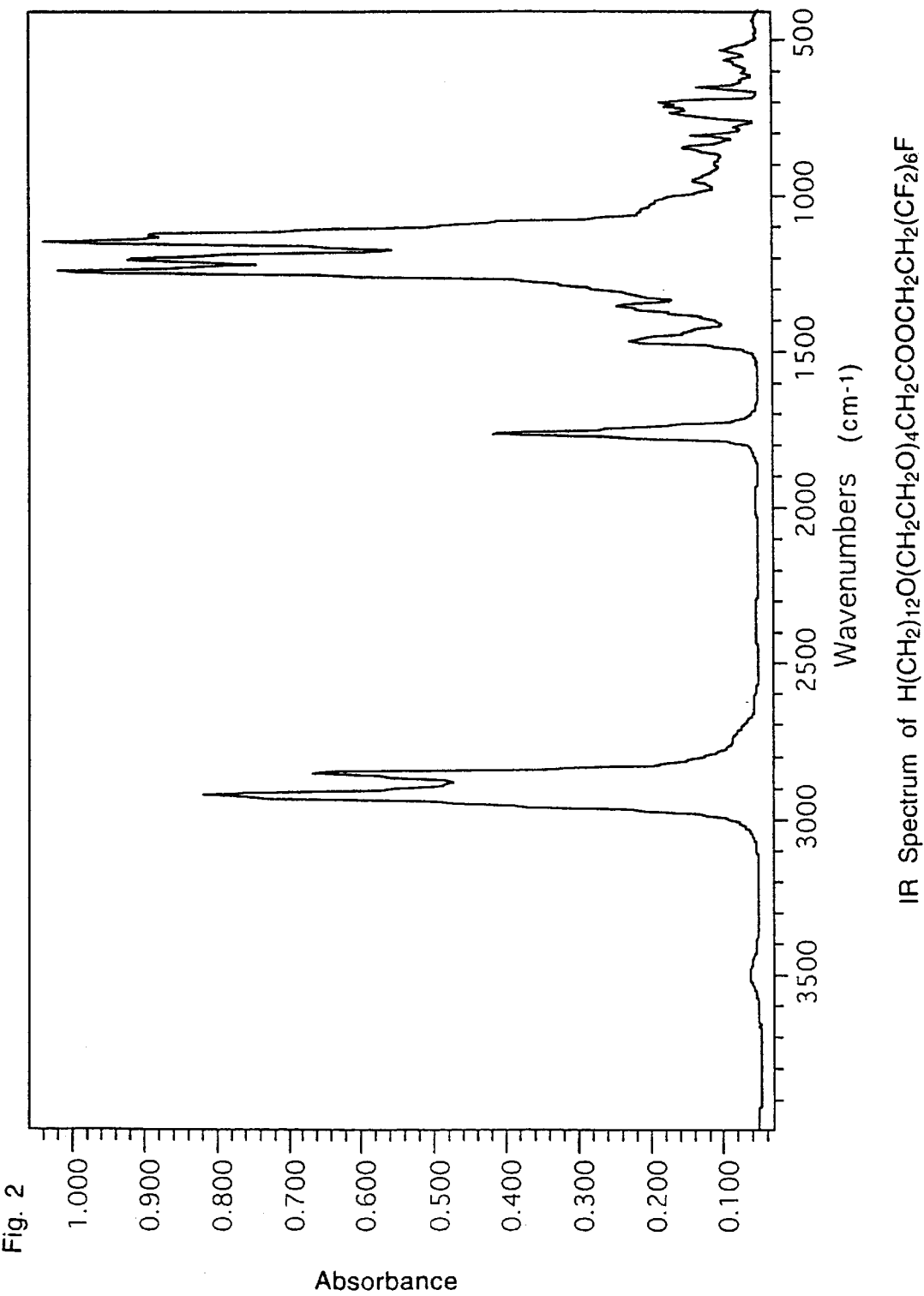
Fig. 2  IR Spectrum of H(CH$_2$)$_{12}$O(CH$_2$CH$_2$O)$_4$CH$_2$COOCH$_2$CH$_2$(CF$_2$)$_6$F

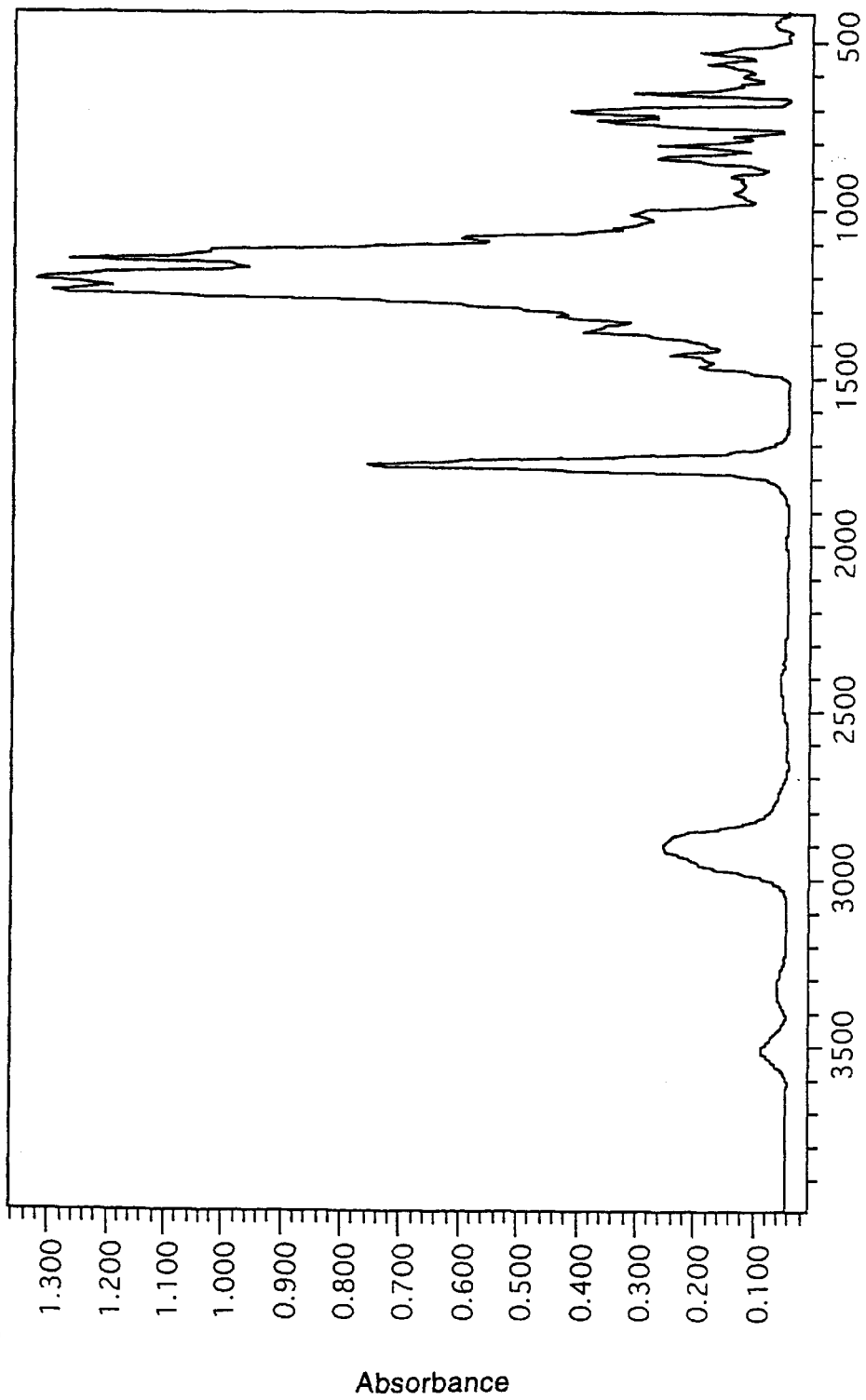
Fig. 3  IR Spectrum of $F(CF_2)_6CH_2CH_2OCOCH_2O(CH_2CH_2O)_3CH_2COOCH_2CH_2(CF_2)_6F$

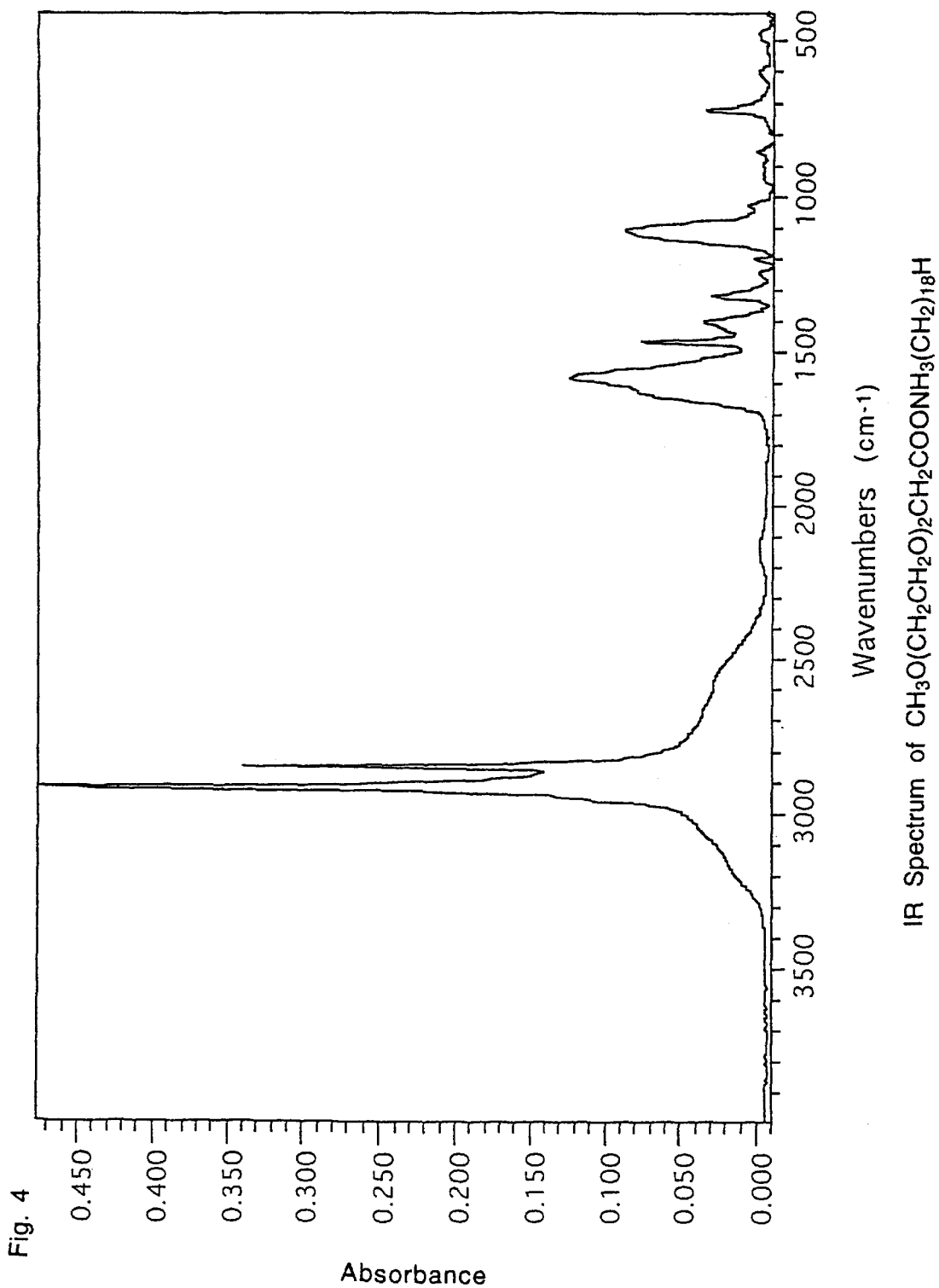
Fig. 4 — IR Spectrum of $CH_3O(CH_2CH_2O)_2CH_2COONH_3(CH_2)_{18}H$

LUBRICATING AGENT AND MAGNETIC RECORDING MEDIUM COMPRISING THE SAME

This application is a divisional of application Ser. No. 08/708,542, filed on Sep. 5, 1996 now U.S. Pat. No. 5,759,968, the entire contents of which are hereby incorporated by reference.

FIELD OF THE INVENTION

The present invention relates to a lubricating agent which makes it possible to slide two contacting solids over each other with low friction and low wear in no relationship to high or low speed and high or low load.

DESCRIPTION OF RELATED ARTS

The hardening of the solid surface and the development of lubricants have been made for the purpose of sliding two contacting solids (namely, two contacting articles) over each other with low friction and low wear to extend the utilization time of apparatus and device. In the field of an office automation (OA) apparatus, the requirement for miniaturization is particularly strong and a precise mechanism has been employed at the sliding part every year. It is required for the future apparatus, wherein precision parts slide continuously or intermittently under various environments, to reduce a friction and wear at the beginning of the sliding, after the completion of the sliding or at the time of the sliding. In a protective lubricating system, there has hitherto been provided a hard surface layer which hardly cause a wear and used a grease-like or oily semisolid or liquid lubricant. Regarding the precise apparatus having sufficient smoothness of the contacting part, there has never been obtained a lubricant which makes it possible to slide two contacting solids over each other with low friction and low wear in spite of high or low speed and high or low load. Therefore, it is impossible to avoid a problem such as a poor start and an accidental rapid increase in friction on the sliding.

For example, in a ferromagnetic metal thin film-type magnetic recording medium produced by coating a ferromagnetic metal or an alloy thereof on a non-magnetic substrate by a vacuum deposition, a higher coercive field and a thinner film of the magnetic layer can be easily attained and high density recording characteristics are better in comparison with a coating-type magnetic recording medium. On the other hand, a binder resin having a sufficient toughness is not used and a surface smoothness of a ferromagnetic thin film layer and a protective layer is good and, therefore, a friction coefficient between the magnetic recording medium and magnetic head becomes large to liable to cause a wear or damage, which results in poor durability and runnability.

Therefore, an improvement of the durability and runnability has been made by providing various lubricants such as a perfluoropolyether lubricant, a carboxylic acid lubricant, a partially fluorinated carboxylic acid lubricant on the ferromagnetic metal thin film layer (e.g. Japanese Patent Kokai Publication Nos. 236118/1987, 308242/1989, 210615/1990 and 65352/1995).

Also in the coating-type magnetic recording medium wherein magnetic powder is bonded with a resin, the high-density recording has made good progress, and it has been required to use the above fluorine-containing lubricant as an excellent lubricant instead of a conventional hydrocarbon lubricant or silicone lubricant.

In order to contain the fluorine-containing lubricant into the magnetic layer or to adhere the fluorine-containing lubricant to the surface of the magnetic layer or protective film, the lubricant must be dissolved in a fluorine-containing organic solvent and then subjected to an operation such as coating, immersion and spraying. However, the fluorine-containing organic solvent has the problems that the solvent leads to an environmental disruption such as the depletion of the ozone layer and that a cost for recovering the solvent is required because the solvent is expensive.

SUMMARY OF THE INVENTION

An object of the present invention is to provide a lubricating agent which makes it possible to slide two contacting solid materials over each other with low friction and low wear in spite of high or low speed and high or low load, and which has no deleterious influence on the environment, in the future precision apparatus wherein the smoothing at the contacting part has made good progress.

The present inventors have intensively studied so as to achieve the above object. As a result, it has been found that it is possible to slide two contacting solids over each other with low friction and low wear by using a lubricating agent comprising at least one alkylene oxide derivative having an alkylene oxide group and an ester moiety or an ammonium salt moiety, which is represented by the following general formula (1), (2), (3) or (4):

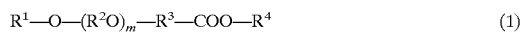
$$R^1\text{—}O\text{—}(R^2O)_m\text{—}R^3\text{—}COO\text{—}R^4 \quad (1)$$

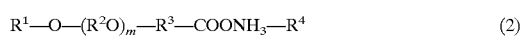
$$R^1\text{—}O\text{—}(R^2O)_m\text{—}R^3\text{—}COONH_3\text{—}R^4 \quad (2)$$

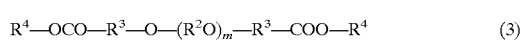
$$R^4\text{—}OCO\text{—}R^3\text{—}O\text{—}(R^2O)_m\text{—}R^3\text{—}COO\text{—}R^4 \quad (3)$$

$$R^4\text{—}NH_3OCO\text{—}R^3\text{—}O\text{—}(R^2O)_m\text{—}R^3\text{—}COONH_3\text{—}R^4 \quad (4)$$

wherein $R^1$ is a hydrocarbon group having 1 to 26 carbon atoms or a hydrogen atom, $R^2$ is a hydrocarbon group having 1 to 6 carbon atoms, $R^3$ is a hydrocarbon group having 1 to 26 carbon atoms, $R^4$ is a hydrocarbon or fluorocarbon group having 1 to 26 carbon atoms, and m is from 1 to 12.

Since the alkylene oxide derivative of the present invention has an alkylene oxide group and an ester moiety or an ammonium salt moiety in the molecule, the derivative has strong absorptivity to the ferromagnetic metal thin film and the protective film so that the derivative can exist stably. As a result, it shows an excellent sliding durability.

BRIEF DESCRIPTION OF THE DRAWINGS

FIG. 1 is an IR spectrum chart of the alkylene oxide derivative 1 produced in Preparative Example 1.

FIG. 2 is an IR spectrum chart of the alkylene oxide derivative 3 produced in Preparative Example 3.

FIG. 3 is an IR spectrum chart of the alkylene oxide derivative 4 produced in Preparative Example 4.

FIG. 4 is an IR spectrum chart of the alkylene oxide derivative 11 produced in Preparative Example 11.

DETAILED DESCRIPTION OF THE INVENTION

The $R^1$ group in the alkylene oxide derivative is a hydrogen atom or a hydrocarbon group having 1 to 26 carbon atoms, preferably 1 to 18 carbon atoms. The structure of the hydrocarbon group may be straight-chain, branched or cyclic. An aliphatic straight-chain or branched hydrocarbon group is preferred. Among them, an aliphatic straight-chain hydrocarbon is particularly preferred.

The $R^2$ group in the alkylene oxide derivative is a hydrocarbon group having 1 to 6 carbon atoms, preferably 1 to 4 carbon atoms. The structure of the hydrocarbon group may be straight-chain, branched or cyclic. An aliphatic straight-chain or branched hydrocarbon group is preferred. Among them, an aliphatic straight-chain hydrocarbon is particularly preferred.

The $R^3$ group in the alkylene oxide derivative is a hydrocarbon group having 1 to 26 carbon atoms, preferably 1 to 18 carbon atoms. The structure of the hydrocarbon group may be straight-chain, branched or cyclic. An aliphatic straight-chain or branched hydrocarbon group is preferred. Among them, an aliphatic straight-chain hydrocarbon is particularly preferred.

The $R^4$ group in the alkylene oxide derivative is a fluorocarbon group or hydrocarbon group having 1 to 26 carbon atoms, preferably 1 to 18 carbon atoms. The $R^4$ group is preferably the fluorocarbon group. While the fluorocarbon group may be one in which hydrogen-containing organic compound (e.g. hydrocarbon) is partially fluorinated, it is preferably one which is completely fluorinated. Preferred examples of the fluorocarbon group include perfluoroalkyl chain and perfluoropolyether group. The structure of the hydrocarbon group and fluorocarbon group may be straight-chain, branched or cyclic. An aliphatic straight-chain or branched $R^4$ group is preferred. Among them, an aliphatic straight-chain $R^4$ is particularly preferred.

When the fluorocarbon group is bonded to an ester moiety (in general formulas (1) and (3)), it is preferred to bond the fluorocarbon group to the ester moiety through a —$(CH_2)_n$— chain, not to bond the fluorocarbon group directly to the ester moiety, in order to improve a hydrolytic resistance. The number of n in the —$(CH_2)_n$— chain is preferably at least 1, more preferably at least 2, in order to obtain the high hydrolytic resistance. Since the fluorocarbon group is bonded to the ester moiety through the —$(CH_2)_n$— chain, the high electronegativity of the fluorine atom is inhibited by the —$(CH_2)_n$— chain. As a result, the hydrolytic resistance of the ester moiety is improved.

It is considered that an influence of the chain length of the fluorocarbon group on solubility is small because a chain of the fluorocarbon group shrinks in a general-purpose organic solvent. However, in order to obtain lubricating properties possessed by the fluorine atom, the number of constituent carbons bonding to the fluorine atom is preferably at least 4, particularly at least 6.

The numeral value of m in the alkylene oxide derivative is from 1 to 12, preferably from 1 to 6. When m is 0, the absorptivity of the alkylene oxide group to the magnetic layer may not be sufficiently exhibited. When m is larger than 12, the effect is saturated and, furthermore, the viscosity becomes high and adhesion between objects is liable to arise.

The alkylene oxide derivative may have a functional group (e.g. —OH, —COOH, —$NH_2$, —Cl, —SH, and an epoxy group) at one end or both ends of molecule, or it may contain an element other than C, H, O, N and F (e.g. N, S, and P) in the molecule.

The alkylene oxide derivative may be synthesized by any process. Examples of an industrially effective synthesis process include a process of reacting a functional group of an alkylene-oxidated material having a hydroxyl group, a carboxyl group or an amino group with a functional group of a fluorocarbon material having a hydroxyl group, a carboxyl group or an amino group and chemically bonding them through an ester linkage, an ammonium salt or the like.

The sliding characteristics of the alkylene oxide derivative of the present invention can be improved by adding an aliphatic amine represented by the following general formula (5):

$$R^5N(R^6)R^7 \qquad (5)$$

wherein $R^5$ is a hydrocarbon group having 1 to 26 carbon atoms; and each of $R^6$ and $R^7$ is a hydrocarbon group having 1 to 26 carbon atoms or a hydrogen atom.

The total number of $R^5$, $R^6$ and $R^7$ is at least 12, preferably from 12 to 26. A molar ratio of the aliphatic amine to the alkylene oxide derivative is preferably 0.01:1 to 100:1, more preferably 0.1:1 to 10:1.

One example of the aliphatic amine is one wherein $R^5$ is the hydrocarbon group and each of $R^6$ and $R^7$ is the hydrogen atom.

The present invention is characterized by using the above compound as the lubricating agent (namely, lubricant). The other general lubricant (e.g. a fatty acid or a metal salt thereof, a fatty acid ester, an aliphatic amide, an aliphatic alcohol, a monosulfide, a paraffin, a silicone compound, an ester of aliphatic compound and fluoride compound, a perfluoropolyether, and polytetrafluoroethylene) may be optionally used in combination with the lubricating agent. In this case, a molar ratio of the other general lubricant to the alkylene oxide derivative is preferably 0.01:1 to 100:1, more preferably 0.1:1 to 10 to 1.

A phosphorus-containing high-pressure agent (e.g. trioleyl phosphate), a sulfur-containing high-pressure agent (e.g. benzyl disulfide), a halogen-containing high-pressure agent (e.g. allyl bromide) and an organic metal high-pressure agent (e.g. zinc diisobutyldithiophosphate) may be used in combination.

In the present invention, in order to provide the lubricant on the magnetic layer or protective film layer, the lubricant is dissolved in the general-purpose solvent (e.g. an alcohol, a hydrocarbon, a ketone, and an ether) and the resultant lubricant solution is coated or sprayed on the previously formed magnetic layer or protective film layer, followed by drying, or the magnetic layer or protective film layer is immersed in the above lubricant solution, followed by drying.

When the magnetic layer is composed of a ferromagnetic metal thin film, a protective film of carbon (in the form of diamond or amorphous carbon), silicon oxide, zirconium oxide, chromium oxide or organic compound may be provided on the thin film by vacuum deposition, sputtering, plasma and the like. Alternatively, a protective film obtained by containing a fluorine or silicon atom in the above protective film material such as carbon may be provided. The ferromagnetic metal thin film may be one wherein a trace amount of water is adhered to the surface, or one wherein a benzotriazole rust preventive is applied on the surface.

The surface of a DLC (diamond-like carbon) protective film may be subjected to an oxygen and ammonia plasma treatment. Chemical active species in plasma can be accumulated while cleaning the surface of the protective film by subjecting to a plasma treatment. Therefore, the lubricant can exist more stably without decreasing the hardness of the protective film. Also, the lubricant can exist stably by subjecting to an ultraviolet irradiation treatment or a heat treatment. These treatments may be conducted before adhering the lubricant, or after adhering the lubricant. Also, they may be conducted, after the lubricant is adhered and then excess lubricant is washed with the solvent.

In the coating-type magnetic recording medium, a magnetic layer containing a lubricant may be formed by mixing the lubricant with a magnetic paint comprising a general-purpose solvent and applying the magnetic paint on a non-magnetic substrate, in addition to the above adhesion process having coating, spraying or immersion. A layer containing the lubricant may be further formed on and adhered to the resultant magnetic layer by repeating above coating, spraying or immersion. After the adhesion, an excessive lubricant may be washed with the solvent. It is also possible to contain the lubricant in a side opposite to the magnetic layer and to transfer the lubricant to a magnetic layer side.

Examples of the general-purpose organic solvent include hexane, heptane, octane, decane, dodecane, benzene, toluene, xylene, cyclohexane, methyl ethyl ketone, methyl isobutyl ketone, methanol, ethanol, isopropanol, diethyl ether, tetrahydrofuran, and cyclohexanone.

An amount of the lubricant applied onto the ferromagnetic metal thin film or the protective layer is preferably from 0.5 to 20 mg per 1 m$^2$ of the surface of the thin film or protective layer. In case of the coating-type magnetic recording medium, an amount of the lubricant contained in the magnetic layer is preferably from 10 to 100 mg/m$^2$. When the amount is too small, it is difficult to adhere the lubricant uniformly on the thin film surface and the still durability can not be sufficiently improved. On the other hand, when the amount is too large, undesirably the magnetic head may adhere to the ferromagnetic metal thin film.

An amount of the lubricant can be determined, for example, by immersing a tape having the lubricant coating in a solvent overnight to extract the lubricant with the solvent, and subjecting to a gas chromatography or liquid column chromatography. In case of the coating-type magnetic recording medium, the lubricant is maintained on the magnetic layer surface or in vacancies in the magnetic layer. Since the lubricating characteristics mainly mean the lubricant extracted by immersing in the solvent, the amount of extracted lubricant can be referred to as a content of the lubricant for the coating-type magnetic recording medium.

In the magnetic recording medium of the present invention, a plastic (e.g. polyethylene terephthalate, polyethylene naphthalate, polycarbonate, polyamide, polyimide, and polyvinyl chloride), a glass, an aluminum alloy, a titanium alloy and the like are preferably used as the non-magnetic substrate. The non-magnetic substrate may have any form such as a tape, a sheet, a disc and a card and may have a projection on the surface.

In the ferromagnetic metal thin film type magnetic recording medium, a thin film made of various ferromagnetic materials (e.g. Co, Ni, Fe, Co—Ni, Co—Cr, Co—P, Co—Ni—P, Fe—Co—B, Fe—Co—Ni, Co—Ni—Fe—B, Fe—Ni, Fe—Co, Co—Pt, Co—Ni—Pt and a mixture of these materials and oxygen) is formed on one surface or both surfaces of the non-magnetic substrate by using a process of a vacuum deposition, an ion plating, a sputtering, a plating and the like. A film thickness of the ferromagnetic metal thin film thus formed is preferably from about 0.03 to about 1 $\mu$m.

In the coating-type magnetic recording medium, a magnetic paint containing magnetic powder and a binder resin is applied on one surface or both surfaces of the non-magnetic substrate to form a magnetic layer having a film thickness of about 0.05 to about 10 $\mu$m. Various additives such as fillers, antistatic agents, dispersants and colorants, which have hitherto been known, can be optionally contained in the magnetic paint.

As the magnetic powder, there can be widely used iron oxides having the intermediate oxidized state between $\gamma$-Fe$_2$O$_3$ and Fe$_3$O$_4$ or $\gamma$-Fe$_2$O$_3$ and Fe$_3$O$_4$, oxide magnetic powder (e.g. Co-containing $\gamma$-Fe$_2$O$_3$, Co-containing $\gamma$-Fe$_3$O$_4$, CrO$_2$, and barium ferrite), metal magnetic powder (e.g. Fe, Co, and Fe—Ni—Cr alloy) and nitride magnetic powder (e.g. iron nitride). In acicular magnetic powder, an average particle size (major axis) is preferably from about 0.05 to about 1 $\mu$m and an average axis ratio (average major axis/average minor axis) is preferably from about 5 to about 10. In case of platelet magnetic powder, an average diameter (major axis) is preferably from about 0.07 to about 0.3 $\mu$m.

As the binder resin, for example, there can be preferably used those which are usually used as a binder of the magnetic recording material, such as a vinyl chloride-vinyl acetate copolymer, a cellulose resin, a polyurethane resin, a polyester resin, a polyvinyl butyrate resin, a polyacrylic resin, an epoxy resin, a phenol resin, and a polyisocyanate compound.

The lubricant may be contained in the protective layer or may be provided on the surface of the protective layer. The thickness of the protective layer is usually from 1 to 100 nm.

In the magnetic recording medium of the present invention having the magnetic layer on only one surface of the non-magnetic material, a back coat layer may be provided on the opposite surface. The back coat layer is formed by mixing and dispersing non-magnetic powder (e.g. carbon black, and calcium carbonate) and a binder resin (e.g. a vinyl chloride-vinyl acetate copolymer, a polyurethane resin, and a cellulose resin) in an organic solvent to prepare a paint for the back coat layer and applying the paint on the opposite surface of the non-magnetic substrate, followed by drying.

As described above, according to the present invention, there could be obtained a lubricating agent which makes it possible to slide two contacting solids over each other with low friction and low wear in spite of high or low speed and high or low load, and which has no deleterious influence on the environment.

PREFERRED EMBODIMENT OF THE INVENTION

The present invention will be illustrated by the following Examples which do not limit the present invention. A magnetic recording medium described in Examples is a typical one. The use, the production process and the substance are illustrative and not restrictive. The alkylene oxide derivatives 1 to 12 used in the Examples are produced by the following Preparative Examples 1 to 12, respectively.

A Fourier transform infrared spectrometer (manufactured by Mattson Co., model PI-1000) was used for the identification of resultant alkylene oxide derivatives.

PREPARATIVE EXAMPLE 1

To a mixture of 2-[2-(2-methoxyethoxy)ethoxy]acetic acid (1 mol) having a carboxyl group at one molecular end and 2-perfluorohexylethanol (1 mol), sodium p-toluenesulfonate (5 mmol) was added. Then, the mixture was reacted at 200° C. for 6 hours while separating the resultant water with a Dean-Stark water separator. After air-cooling, the reaction product was washed with an aqueous sodium bicarbonate solution and purified by recrystallization or distillation to produce an alkylene oxide derivative 1 represented by the following chemical formula:

PREPARATIVE EXAMPLE 2

In the same manner as in Preparative Example 1 except for using 2-(2-methoxyethoxy)acetic acid (1 mol) instead of 2-[2-methoxyethoxy)ethoxy]acetic acid, the reaction was conducted to produce an alkylene oxide derivative 2 represented by the following chemical formula:

$$CH_3OCH_2CH_2OCH_2COOCH_2CH_2(CF_2)_6F$$

PREPARATIVE EXAMPLE 3

In the same manner as in Preparative Example 1 except for using 2-(lauroxy-tetraethoxy)acetic acid (1 mol) instead of 2-[2-(2-methoxyethoxy) ethoxy]acetic acid, the reaction was conducted to produce an alkylene oxide derivative 3 represented by the following chemical formula:

$$H(CH_2)_{12}O(CH_2CH_2O)_4CH_2COOCH_2CH_2(CF_2)_6F$$

PREPARATIVE EXAMPLE 4

In the same manner as in Preparative Example 1 except for using polyethylene glycol biscarboxymethyl ether (0.5 mol) instead of 2-[2-(2-methoxyethoxy)ethoxy]acetic acid, the reaction was conducted to produce an alkylene oxide derivative 4 represented by the following chemical formula:

$$F(CF_2)_6CH_2CH_2OCOCH_2(OCH_2CH_2)_3OCH_2COOCH_2CH_2(CF_2)_6F$$

PREPARATIVE EXAMPLE 5

In the same manner as in Preparative Example 1 except for using 3,3'-oxybis2,2'-dimethylpropanoic acid) (0.5 mol) instead of 2-[2-(2-methoxyethoxy)ethoxy]acetic acid, the reaction was conducted to produce an alkylene oxide derivative 5 represented by the following chemical formula:

$$F(CF_2)_6CH_2CH_2OCOC(CH_3)_2CH_2OCH_2C(CH_3)_2COOCH_2CH_2(CF_2)_6F$$

PREPARATIVE EXAMPLE 6

In the same manner as in Preparative Example 1 except for using stearyl alcohol (1 mol) instead of 2-perfluorohexylethanol, the reaction was conducted to produce an alkylene oxide derivative 6 represented by the following chemical formula:

$$CH_3O(CH_2CH_2O)_2CH_2COO(CH_2)_{18}H$$

PREPARATIVE EXAMPLE 7

2-[2-(2-methoxyethoxy)ethoxy]acetic acid (1 mol) was reacted with 1H,1H-pentadecafluorooctylamine at 120° C. for 6 hours. The reaction product was purified by recrystallization or distillation to give an alkylene oxide derivative 7 represented by the following chemical formula:

$$CH_3O(CH_2CH_2O)_2CH_2COONH_3CH_2(CF_2)_7F$$

PREPARATIVE EXAMPLE 8

In the same manner as in Preparative Example 7 except for using 2-(2-methoxyethoxy)acetic acid (1 mol) instead of 2-[2-methoxyethoxy)ethoxy]acetic acid, the reaction was conducted to produce an alkylene oxide derivative 8 represented by the following chemical formula:

$$CH_3OCH_2CH_2OCH_2COONH_3CH_2(CF_2)_7F$$

PREPARATIVE EXAMPLE 9

In the same manner as in Preparative Example 7 except for using 2-(lauroxytetraethoxy)acetic acid (1 mol) instead of 2-[2-(2-methoxyethoxy)ethoxy]acetic acid, the reaction was conducted to produce an alkylene oxide derivative 9 represented by the following chemical formula:

$$H(CH_2)_{12}O(CH_2CH_2O)_4CH_2COONH_3CH_2(CF_2)_7F$$

PREPARATIVE EXAMPLE 10

In the same manner as in Preparative Example 7 except for using polyethylene glycol biscarboxymethyl ether (0.5 mol) instead of 2-[2-(2-methoxyethoxy)ethoxy]acetic acid, the reaction was conducted to produce an alkylene oxide derivative 10 represented by the following chemical formula:

$$F(CF_2)_7CH_2NH_3OCOCH_2(OCH_2CH_2)_3OCH_2COONH_3CH_2(CF_2)_7F$$

PREPARATIVE EXAMPLE 11

In the same manner as in Preparative Example 7 except for using stearylamine (1 mol) instead of 1H,1H-pentadecafluorooctylamine, the reaction was conducted to produce an alkylene oxide derivative 11 represented by the following chemical formula:

$$CH_3O(CH_2CH_2O)_2CH_2COONH_3(CH_2)_{18}H$$

PREPARATIVE EXAMPLE 12

In the same manner as in Preparative Example 10 except for using stearylamine (1 mol) instead of 1H,1H-pentadecafluorooctylamine, the reaction was conducted to produce an alkylene oxide derivative 12 represented by the following chemical formula:

$$H(CH_2)_{18}NH_3OCOCH_2(OCH_2CH_2)_3OCH_2COONH_3(CH_2)_{18}H$$

EXAMPLES 1 to 18 AND COMPARATIVE EXAMPLES 1 TO 3

Co was obliquely vapor-deposited on a polyethylene terephthalate film having a thickness of 6 $\mu$m under an oxygen atmosphere to form a ferromagnetic metal thin film of Co—O having a thickness of 0.15 $\mu$m on the polyethylene terephthalate film. Then, a DLC (diamond-like carbon) protective film (thickness: 20 nm) was formed on the ferromagnetic metal thin film by using RF (radio frequency) of 13.56 MHz, ethylene as a monomer gas and hydrogen as a carrier gas according to a plasma polymerization process, and the resultant polyethylene terephthalate film was cut into tapes having a width of 8 mm.

The lubricants shown in the following Table 1 were used for comparison. The lubricants in Examples and Comparative Examples shown in Table 2 were dissolved in a mixture of n-hexane, methyl ethyl ketone and isopropyl alcohol [n-hexane:methyl ethyl ketone:isopropyl alcohol=7:2:1 (weight ratio)] so that the concentration of the resultant solution became 0.2% by weight (the lubricants of Comparative Examples 1 and 2 were dissolved in 1,1,2-trifluoro-1,2,2-trichloroethane in the concentration of 0.2% by weight). The above tape was immersed in this lubricant solution, followed by drying to prepare a video tape having a lubricant coat (lubricant amount: 6 mg/m$^2$) on a DLC protective film. In Examples 13–18, the aliphatic amines shown in Table 2 were used in an aliphatic amine/alkylene oxide derivative molar ratio of 1:1.

Lubrication properties of the respective video tapes were evaluated by measuring the still durability and the friction coefficient. Also, the solubility of the lubricants used in Examples and Comparative Examples in a general-purpose solvent was measured. The results are shown in Table 2. The still durability, the friction coefficient and the solubility were measured according to the following method.

TABLE 1

| Lubricant A: | Fluorinated ether compound, FOMBLIN Z DOL (manufactured by Montefluos Co., average molecular weight: about 2000) |
|---|---|
| Lubricant B: | Fluorinated ether compound, FOMBLIN Z DIAC (manufactured by Montefluos Co., average molecular weight: about 2000) |
| Lubricant C: | Fluorinated ester compound, $F(CF_2)_6CH_2CH_2OCO(CH_2)_{17}H$ |

<Still Durability>

The video tape is set on a cylinder for 8 mm tape having a diameter of 4 cm at a winding angle of 220° under 20° C. and 50% RH, and a sine wave having a wavelength of 1.6 µm recorded under the condition of a tape-magnetic head relative speed of 11.3 m/second and a tape tension of 12.5 gf/cm, thereby measuring a reproducing output and a cylinder load at the time of still under a still mode. A time required for the reproducing output to decrease from an initial value by 6 dB is defined as a still life.

<Friction coefficient>

A reciprocating sliding test sliding a video tape on stainless steel pin is conducted 20 times at 20° C. and 50% RH under the conditions of a sliding speed of 1 m/minute, a sliding distance of 5 cm and a tape tension of 20 g, thereby measuring a friction coefficient after reciprocating 20 times.

<Solubility>

Using a mixture of n-hexane, methyl ethyl ketone and isopropyl alcohol (=7:2:1) as a general-purpose solvent, the lubricant is added to this solvent in small portions, followed by stirring. A solubility is evaluated by the following criteria:

○: An amount of the dissolved lubricant is at least 0.05% by weight.

X: An amount of the dissolved lubricant is smaller 0.05% by weight.

EXAMPLES 19 to 36 AND COMPARATIVE EXAMPLES 4 TO 6

Co—Ni was obliquely vapor-deposited on a polyethylene terephthalate film having a thickness of 10 µm under an oxygen atmosphere to form a ferromagnetic metal thin film of Co—Ni—O [Co:Ni (weight ratio)=80:20] having a thickness of 0.15 µm on the polyethylene terephthalate film. Then, the resultant polyethylene terephthalate film was cut into tapes having a width of 8 mm.

Then, in the same manner as in the above Examples and Comparative Examples, the lubricant was dissolved in a mixture of n-hexane, methyl ethyl ketone and isopropyl alcohol [n-hexane:methyl ethyl ketone:isopropyl alcohol= 7:2:1 (weight ratio)] so that the concentration of the resultant lubricant solution became 0.2% by weight (the lubricants of Comparative Examples 4 and 5 were dissolved in 1,1,2-trifluoro-1,2,2-trichloroethane in the concentration of 0.2% by weight). The above tape was immersed in the lubricant solution, followed by drying to prepare a video tape having a lubricant coat (lubricant amount: 8 mg/m$^2$) on the ferromagnetic metal thin film. In Examples 31–36, the aliphatic amines shown in Table 3 were used in an aliphatic amine/alkylene oxide derivative molar ratio of 1:1.

According to the same manner as described above, the still durability and the friction coefficient of the video tape were evaluated. The results are shown in Table 3.

EXAMPLES 37 TO 54 AND COMPARATIVE EXAMPLES 7 TO 9

A composition comprising 100 parts by weight of α-Fe magnetic powder (coercive force: 1500 oersted, saturation magnetization: 120 emu/g), 20 parts by weight of a vinyl chloride-vinyl acetate-vinyl alcohol copolymer (VAGH, manufactured by UCC Co.), 5 parts by weight of a polyfunctional isocyanate compound, 3 parts by weight of carbon black, 3 parts by weight of α-Al$_2$O$_3$ powder, 2 parts by weight of myristic acid, 150 parts by weight of cyclohexane and 130 parts by weight of toluene was mixed in a ball mill for 72 hours to prepare a magnetic paint. The magnetic paint was applied on a polyethylene terephthalate film having a thickness of 15 µm so that a thickness after drying became 5 µm, followed by drying to form a magnetic layer. After calendering, the resultant polyethylene terephthalate film was cut into tapes having a width of 8 mm.

Then, in the same manner as in the above Examples and Comparative Examples, the lubricant shown in Table 4 was dissolved in a mixture of n-hexane, methyl ethyl ketone and isopropyl alcohol [n-hexane:methyl ethyl ketone:isopropyl alcohol=7:2:1 (weight ratio)] so that the concentration resultant lubricant solution became 0.2% by weight (the lubricants of Comparative Examples 7 and 8 were dissolved in 1,1,2-trifluoro-1,2,2-trichloroethane in the concentration of 0.2% by weight). The above tape was immersed in the lubricant solution, followed by drying to prepare a video tape having a lubricant coat (lubricant amount: 50 mg/m$^2$) on a ferromagnetic metal thin film. In Examples 49–54, the aliphatic amines shown in Table 4 were used in an aliphatic amine/alkylene oxide derivative molar ratio of 1:1.

In the same manner as in the above, the still durability and the friction coefficient of the video tape were evaluated. The results are shown in Table 4.

As is apparent from the results of Tables 2 to 4, all video tapes comprising the lubricants used in Examples 1 to 54 show a long still life and a small friction coefficient in comparison with those comprising the conventional lubricants used in Comparative Examples 1 to 9. The lubricant of the present invention is superior in solubility and lubricating properties.

TABLE 2

|  | Lubricant | | Still | | |
|---|---|---|---|---|---|
|  | Alkylene oxide derivative | Aliphatic amine | Still durability (minute) | Friction coefficient | Solubility |
| Example 1 | 1 | — | >180 | 0.23 | ○ |
| Example 2 | 2 | — | >180 | 0.24 | ○ |
| Example 3 | 3 | — | >180 | 0.26 | ○ |

TABLE 2-continued

| | Lubricant | | Still durability (minute) | Friction coefficient | Solubility |
|---|---|---|---|---|---|
| | Alkylene oxide derivative | Aliphatic amine | | | |
| Example 4 | 4 | — | >200 | 0.28 | ○ |
| Example 5 | 5 | — | >180 | 0.27 | ○ |
| Example 6 | 6 | — | >180 | 0.24 | ○ |
| Example 7 | 7 | — | >180 | 0.23 | ○ |
| Example 8 | 8 | — | >180 | 0.23 | ○ |
| Example 9 | 9 | — | >200 | 0.26 | ○ |
| Example 10 | 10 | — | >200 | 0.27 | ○ |
| Example 11 | 11 | — | >200 | 0.21 | ○ |
| Example 12 | 12 | — | >200 | 0.26 | ○ |
| Example 13 | 1 | $H(CH_2)_{18}NH_2$ | >200 | 0.20 | ○ |
| Example 14 | 1 | $H(CH_2)_8CH{=}CH(CH_2)_8NH_2$ | >180 | 0.23 | ○ |
| Example 15 | 3 | $H(CH_2)_{18}NH_2$ | >200 | 0.23 | ○ |
| Example 16 | 4 | $H(CH_2)_{18}NH_2$ | >200 | 0.26 | ○ |
| Example 17 | 7 | $H(CH_2)_{18}NH_2$ | >180 | 0.22 | ○ |
| Example 18 | 11 | $H(CH_2)_{18}NH_2$ | >200 | 0.23 | ○ |
| Comparative Example 1 | Lubricant A | | 125 | 0.27 | X |
| Comparative Example 2 | Lubricant B | | 100 | 0.29 | X |
| Comparative Example 3 | Lubricant C | | 120 | 0.27 | ○ |

TABLE 3

| | Lubricant | | Still durability (minute) | Friction coefficient |
|---|---|---|---|---|
| | Alkylene oxide derivative | Aliphatic amine | | |
| Example 19 | 1 | — | >120 | 0.22 |
| Example 20 | 2 | — | >120 | 0.24 |
| Example 21 | 3 | — | >120 | 0.27 |
| Example 22 | 4 | — | >140 | 0.28 |
| Example 23 | 5 | — | >120 | 0.27 |
| Example 24 | 6 | — | >120 | 0.26 |
| Example 25 | 7 | — | >140 | 0.23 |
| Example 26 | 8 | — | >120 | 0.23 |
| Example 27 | 9 | — | >140 | 0.27 |
| Example 28 | 10 | — | >140 | 0.26 |
| Example 29 | 11 | — | >140 | 0.23 |
| Example 30 | 12 | — | >120 | 0.25 |
| Example 31 | 1 | $H(CH_2)_{18}NH_2$ | >140 | 0.22 |
| Example 32 | 1 | $H(CH_2)_8CH{=}CH(CH_2)_8NH_2$ | >120 | 0.24 |
| Example 33 | 3 | $H(CH_2)_{18}NH_2$ | >120 | 0.24 |
| Example 34 | 4 | $H(CH_2)_{18}NH_2$ | >120 | 0.26 |
| Example 35 | 7 | $H(CH_2)_{18}NH_2$ | >120 | 0.23 |
| Example 36 | 11 | $H(CH_2)_{18}NH_2$ | >120 | 0.23 |
| Comparative Example 4 | Lubricant A | | 55 | 0.27 |
| Comparative Example 5 | Lubricant B | | 70 | 0.29 |
| Comparative Example 6 | Lubricant C | | 60 | 0.26 |

TABLE 4

| | Lubricant | | Still durability (minute) | Friction coefficient |
|---|---|---|---|---|
| | Alkylene oxide derivative | Aliphatic amine | | |
| Example 37 | 1 | — | >220 | 0.21 |
| Example 38 | 2 | — | >220 | 0.23 |
| Example 39 | 3 | — | >220 | 0.25 |
| Example 40 | 4 | — | >240 | 0.28 |
| Example 41 | 5 | — | >220 | 0.25 |
| Example 42 | 6 | — | >220 | 0.26 |
| Example 43 | 7 | — | >220 | 0.22 |
| Example 44 | 8 | — | >220 | 0.22 |
| Example 45 | 9 | — | >220 | 0.23 |
| Example 46 | 10 | — | >220 | 0.27 |
| Example 47 | 11 | — | >240 | 0.21 |
| Example 48 | 12 | — | >220 | 0.24 |
| Example 49 | 1 | $H(CH_2)_{18}NH_2$ | >240 | 0.21 |
| Example 50 | 1 | $H(CH_2)_8CH{=}CH(CH_2)_8NH_2$ | >220 | 0.22 |
| Example 51 | 3 | $H(CH_2)_{18}NH_2$ | >220 | 0.23 |
| Example 52 | 4 | $H(CH_2)_{18}NH_2$ | >220 | 0.24 |
| Example 53 | 7 | $H(CH_2)_{18}NH_2$ | >220 | 0.21 |
| Example 54 | 11 | $H(CH_2)_{18}NH_2$ | >240 | 0.23 |
| Comparative Example 7 | Lubricant A | | 105 | 0.26 |
| Comparative Example 8 | Lubricant B | | 60 | 0.25 |
| Comparative Example 9 | Lubricant C | | 120 | 0.25 |

What is claimed is:

1. A magnetic recording medium comprising a non-magnetic substrate, and a magnetic layer provided on at least one surface of the substrate, and a lubricating agent comprising at least one alkylene oxide derivative having an alkylene oxide group and an ester moiety or an ammonium salt moiety, which is represented by the following general formula (2) or (4):

$$R^1{-}O{-}(R^2O)_m{-}R^3{-}COONH_3{-}R^4 \qquad (2)$$

$$R^4{-}NH_3OCO{-}R^3{-}O{-}(R^2O)_m{-}R^3{-}COONH_3{-}R^4 \qquad (4)$$

wherein $R^1$ is a hydrocarbon group having 1 to 26 carbon atoms or a hydrogen atom, $R^2$ is a hydrocarbon group having 1 to 6 carbon atoms, $R^3$ is a hydrocarbon group having 1 to 26 carbon atoms, $R^4$ is a hydrocarbon or fluorocarbon group having 1 to 26 carbon atoms, and m is from 1 to 12, said lubricating agent being in or on the magnetic layer.

2. A magnetic recording medium comprising a non-magnetic substrate, a magnetic layer provided on at least one surface of the substrate, and a lubricating agent comprising:

(A) at least one alkylene oxide derivative having an alkylene oxide group and an ester moiety or an ammonium salt moiety, which is represented by the following general formula (1), (2), (3) or (4):

$$R^1-O-(R^2O)_m-R^3-COO-R^4 \qquad (1)$$

$$R^1-O-(R^2O)_m-R^3-COONH_3-R^4 \qquad (2)$$

$$R^4-OCO-R^3-O-(R^2O)_m-R^3-COO-R^4 \qquad (3)$$

$$R^4-NH_3OCO-R^3-O-(R^2O)_m-R^3-COONH_3-R^4 \qquad (4)$$

wherein $R^1$ is a hydrocarbon group having 1 to 26 carbon atoms or a hydrogen atom, $R^2$ is a hydrocarbon group having 1 to 6 carbon atoms, $R^3$ is a hydrocarbon group having 1 to 26 carbon atoms, $R^4$ is a hydrocarbon or fluorocarbon group having 1 to 26 carbon atoms, and m is from 1 to 12, and (B) at least one aliphatic amine represented by the following general formula (5):

$$R^5N(R^6)R^7 \qquad (5)$$

wherein $R^5$ is a hydrocarbon group having 1 to 26 carbon atoms, and each of $R^6$ and $R^7$ is a hydrocarbon having 1 to 26 carbon atoms or a hydrogen atom, wherein said lubricating agent is in or on the magnetic layer.

3. The magnetic recording medium according to claim 1 or 2, wherein the magnetic recording medium is a ferromagnetic metal thin film-type magnetic recording medium and a coating weight of the lubricating agent is from 0.5 to 20 mg/m².

4. The magnetic recording medium according to claim 3, further comprising a carbon, silicon oxide, zirconium oxide or chromium oxide protective film on a ferromagnetic metal thin film.

5. The magnetic recording medium according to claim 1 or 2, wherein the magnetic recording medium is a coating-type magnetic recording medium and an amount of the lubricating agent contained in the magnetic layer is from 10 to 100 mg/m².

* * * * *